(12) United States Patent
Waters

(10) Patent No.: US 8,075,901 B1
(45) Date of Patent: Dec. 13, 2011

(54) COSMETIC FORMULATION

(76) Inventor: Sheila F. Waters, Washington, DC (US)

( * ) Notice: Subject to any disclaimer, the term of this patent is extended or adjusted under 35 U.S.C. 154(b) by 32 days.

(21) Appl. No.: 12/623,492

(22) Filed: Nov. 23, 2009

(51) Int. Cl.
*A61K 36/328* (2006.01)
*A61K 36/752* (2006.01)
*A61K 36/889* (2006.01)

(52) U.S. Cl. .................. 424/195.17; 424/727; 424/736; 424/748; 424/401

(58) Field of Classification Search .................. None
See application file for complete search history.

(56) References Cited

U.S. PATENT DOCUMENTS

| | | | |
|---|---|---|---|
| 5,658,577 A | 8/1997 | Fowler | |
| 5,997,889 A * | 12/1999 | Durr et al. | 424/401 |
| 6,521,217 B1 | 2/2003 | Luther | |
| 6,582,710 B2 | 6/2003 | Deckers | |
| 6,974,799 B2 | 12/2005 | Lintner | |
| 7,250,174 B2 | 7/2007 | Lee | |
| 7,544,375 B1 | 6/2009 | Bellin | |
| 2006/0018867 A1 | 1/2006 | Kawasaki | |
| 2007/0134195 A1 * | 6/2007 | Ward et al. | 424/74 |
| 2009/0068128 A1 | 3/2009 | Waddington | |
| 2009/0068255 A1 | 3/2009 | Yu | |

* cited by examiner

*Primary Examiner* — Susan Hoffman
(74) *Attorney, Agent, or Firm* — John Gibson Semmes; Law Offices John Gibson Semmes

(57) ABSTRACT

A formulation includes water, shea butter, an emulsifier and an essential oil comprising myrrh. In addition, the formulation can include cocoa butter, coconut oil, kelp powder, and a preservative comprising a mixture of phenoxyethanol, methylparaben, ethylparaben, propylparaben and butylparaben. The formulation can be used for cosmetic applications in which the formulation is applied as a cream to a user's skin.

4 Claims, No Drawings

COSMETIC FORMULATION

BACKGROUND

Different cosmetic formulations are commercially available that include a large number of synthetic substances which can be harmful to persons, particularly persons with sensitive skin.

It would be useful to provide a cosmetic formulation that is formulated with natural substances and has a look, feel, texture and efficacy that is desirable for cosmetic applications.

SUMMARY OF THE INVENTION

A cosmetic formulation comprises water, shea butter, an emulsifier and an essential oil comprising myrrh. In addition, the formulation can comprise cocoa butter, coconut oil, kelp powder, and a preservative comprising a mixture of phenoxyethanol, methylparaben, ethylparaben, propylparaben and butylparaben. Additional essential oils, including orange oil, bergamot oil and sandalwood oil can also be included in the formulation.

The formulation primarily utilizes natural substances and can be used for topical applications to the body of a user for the treatment, prevention and/or improvement of the appearance of the user's skin.

The above and still further objects, features and advantages of the present invention will become apparent upon consideration of the following detailed description. While the detailed description discloses specific details of the invention, it should be understood that variations may exist and would be apparent to those skilled in the art.

DETAILED DESCRIPTION

The present invention relates to a formulation or composition for topical applications to the body of a user for the treatment, prevention and/or improvement of the appearance of the user's skin. The formulation comprises a number of different natural ingredients or substances including, without limitation, filtered or spring water, natural fats such as shea butter and/or cocoa butter, one or more essential oils, and a suitable emulsifier (such as emulsifying wax) to bind the water and oils together. Many or all of the substances that are combined to produce the formulation are generally recognized as safe (GRAS).

The use of one or more natural fats in the formulation provides a number of benefits, including the improvement of skin elasticity and other benefits for the skin. A preferred natural fat for the formulation is shea butter (e.g., unrefined shea butter). Shea butter is a natural fat extracted from the Shea tree. Shea butter is known especially for its cosmetic properties as a moisturizer and emollient. Shea butter is believed to provide a number of beneficial properties including, without limitation, minimization of wrinkles, scars, and stretch marks by enhancing and/or restoring skin elasticity, and for treating acne, severely dry skin, blemishes, dark spots, skin discolorations, and chapped lips. Shea butter is also believed to control or prevent fungal infections, dermatitis, eczema and psoriasis. In addition, shea butter can act as an anti-inflammatory agent and provides protection as a natural sunscreen against ultraviolet light. Shea butter also serves as a softener for skin, hair and nails, and it has a unique aroma that enhances the aesthetic appearance and smell of the formulation.

Another natural fat that can also be used in the formulation is cocoa butter. Cocoa butter is a vegetable fat that is extracted from the cocoa bean. It is believed to provide similar benefits as shea butter with respect to enhancing skin elasticity and minimizing wrinkles and scars, and it further can serve as a natural sunscreen against ultraviolet light. Cocoa butter also has a unique aroma that can enhance the aesthetic smell of the formulation product. Cocoa butter is one of the most stable natural fats known, and it contains natural antioxidants that prevent rancidity and help to give the formulation long storage life.

One or more tropical oils can also be provided in the formulation to provide additional antioxidant properties and also enhance the texture, look, feel and smell of the formulation. A preferred tropical oil for use in the formulation is coconut oil, which is obtained by extraction from the meat of a coconut. Coconut oil acts as a natural skin moisturizer and softener for the formulation.

Other natural fats or oils can also be provided within the formulation that are known for use in cosmetic or other topical skin applications. However, the inventor has determined that the use of shea butter or a combination of shea butter with cocoa butter and/or coconut oil with the further combination of other substances of the formulation provides a unique formulation with unexpected benefits in relation to the look, feel, texture, smell, efficacy and overall aesthetic appearance of the product.

It is desirable to provide one or more essential oils in the formulation to provide an aromatherepeutic component to the formulation as well as further enhance the smell and other aesthetic qualities of the formulation. Preferred essential oils for use in the formulation include orange, bergamot, sandalwood and myrrh.

Myrrh is most preferred as the essential oil because of its anti-inflammatory properties, its efficacy in treating eczema, acne and athlete's foot, and also due to its unique aroma which enhances the aesthetic qualities of the formulation. Myrrh is a resinous material that can be obtained from the dried sap of a number of different trees including, without limitation, *Commiphora myrrha* (native to Yemen, Somalia and parts of Ethiopia) and *Commiphora gileadensis* (native to Jordan).

Other essential oils that have been found beneficial in combining with other substances to obtain the formulation of the invention are orange and bergamot oils. Orange oil is extracted from the rind of orange fruit. It is comprised primarily (90% or greater) of d-limonene. Orange oil acts as an astringent on the skin and is also believed to act as a sedative and promote relaxation in aromatherapy. Bergamot oil is extracted from bergamot oranges and is also believed to act as a sedative and provide a soothing and uplifting feeling in aromatherapy. Bergamot oil is also useful in the treatment of acne.

Sandalwood oil can also be provided in the formulation of the present invention. Sandalwood oil is extracted from the Sandalwood tree. It is also believed to provide a soothing and uplifting feeling in aromatherapy, and it provides antiseptic benefits and treats dry skin.

Other essential oils can also be used in the formulation, depending upon a desired aromatherapeutic other aesthetic effect that is desired for the formulation. Other essential oils that can be used in the formulation include, without limitation, almond, anise, basil, bay, bitter almond, cajeput, camphor, cassia, cedarwood, chamomile, cinnamon, citronella, clove, clove bud, coriander, cypress, eucalyptus, fennel, fir, frankincense, geranium, ginger, grapefruit, jasmine, lavender, lemon, lemongrass, lime, litsea, marigold, marjoram, Melissa, myrtle, neroli, nutmeg, oakmoss, palmorosa, patchouli, pennyroyal, peppermint, pettigrain, pine, rose, rosemary, sage, spearmint, spruce, sweet birch, tangerine, tea tree, vanilla, vetivert, white thyme, wintergreen, and ylang ylang. However, as noted above, the preferred essential oils are myrrh, orange, bergamot and sandalwood, with myrrh being the most preferred.

The formulation further includes water (e.g., filtered or spring water) to provide volume and to reduce the greasy texture of the formulation caused by the natural fats. In addition, a suitable emulsifier, such as an emulsifying wax, is provided in the formulation to bind water and oils together in a suitable emulsion. The emulsifying wax can be a combination of a vegetable oil with a detergent, such as sodium dodecyl sulfate (SDS) or polysorbates. Examples of suitable types of emulsifying waxes that can be used in the formulation include, without limitation, emulsifying waxes comprising cetearyl alcohol and polyoxyethylene sorbitan monostearates commercially available under the tradename Polysorbate 60, and emulsifying waxes comprising cetearyl alcohol and polyoxyethylene ethers commercially available under the tradename Ceteareth 20. Other suitable emulsifiers that can be used in the formulation include bees wax, polysorbate surfactants such as a polyoxyethylene derivative of sorbitan monolaurate (e.g., those commercially available under the tradename Polysorbate 20 or Tween 20), and other types of fragrance oil and/or essential oil modifiers.

A suitable preservative that facilitates an increase in shelf life of the formulation is also preferably provided in the formulation. An example of a suitable preservative is a mixture of phenoxyethanol, methylparaben, ethylparaben, propylparaben and butylparaben, commercially available under the trademark Phenonip. The Phenonip preservative provides protection against the formation of bacteria, mold and yeast within the formulation.

In addition, natural substances that provide phytonutrient properties to the formulation can be provided, such as kelp powder. Other sea weeds other than or in addition to kelp can also be used in the formulation. Kelp is believed to provide nourishment and enhanced regeneration for skin cells.

A food grade colorant, such as FD&C Yellow 5 and/or FD&C Blue 1, can also be provided in the formulation to enchance the aesthetic look and appeal of the formulation. A preferred formulation of the present invention includes shea butter, an emulsifying wax, myrrh and water. The amount of water used in the formulation is preferably within a range from about 35% to about 50% by volume of the formulation (e.g., mL/mL), while the amount of shea butter is preferably from about 25% to about 40% by volume of the formulation. The amount of emulsifying wax used in the formulation is preferably from about 10% to about 20% by volume of the formulation. The amount of myrrh used in the formulation is preferably less than about 1% by volume of the formulation.

In an example embodiment, the formulation includes filtered or spring water, emulsifying wax, shea butter, cocoa butter, coconut oil, kelp powder, Phenonip preservative, myrrh oil, orange oil, bergamot oil and sandalwood oil. In addition, the formulation includes a food grade colorant. The amounts of each of these substances in the formulation is as follows: water in an amount within a range from about 35% to about 50% by volume of the formulation (e.g., mL/mL); emulsifying wax in an amount within a range from about 10% to about 20% by volume of the formulation; shea butter in an amount from about 25% to about 40% by volume of the formulation; cocoa butter in an amount no greater than about 10% by volume of the formulation; coconut oil in an amount no greater than about 5% by volume of the formulation; kelp powder in an amount less than about 1% by volume of the formulation; a preservative such as Phenonip in an amount of less than about 2% (preferably less than about 1%) by volume of the formulation; myrrh oil in an amount of less than about 1% by volume of the formulation; and each of orange oil, bergamot oil and sandalwood oil in an amount of less than about 1% by volume of the formulation.

A preferred cosmetic formulation having a cream-like consistency can be formed having the following components in the following amounts:

| Substance | Amount |
| --- | --- |
| Filtered or Spring Water | 311 mL |
| Emulsifying Wax | 118 mL |
| Unrefined Shea Butter | 237 mL |
| Cocoa Butter | 29.5 mL |
| Coconut Oil | 15 mL |
| Kelp Powder | 4.9 mL |
| Phenonip | 5.48 mL |
| Myrrh | 3 mL |
| Orange Oil | 6 mL |
| Bergamot Oil | 6 mL |
| Sandalwood Oil | 6 mL |

The preferred cosmetic formulation described above will consist essentially of the substances listed in the table, where it is noted that trace amounts of certain other substances (e.g., substances having concentrations no greater than about 1% by volume of the formulation) may be in the formulation without significantly altering the efficacy and functionality of the cosmetic formulation.

One substance that can be added to the formulation that will not affect the overall efficacy of the formulation is a food grade colorant that provides the formulation with an aesthetically pleasing color. An example of a suitable food grade colorant is a combination of FD&C Yellow 5 and FD&C Blue 1. These two colorants can be added in a suitable amount (e.g., 3 drops FD&C Yellow 5 and 2 drops FD&C Blue 1) to the formulation described in the table above to provide the formulation with a green color. The green color for the formulation is believed to provide a soothing visual appeal for the cosmetic formulation, which renders the formulation more aesthetically pleasing for the user.

The formulation described above can be produced in accordance with the invention using the following process. An emulsifying wax (melting point 110° F.-120° F.) is initially melted and combined with cocoa butter and coconut oil in the volumetric amounts as described above. This mixture is further combined with water, the preservative and the essential oils provided in the amounts as noted above. An electric stick blender can be used to beat the mixture together until it is thickened or has a viscosity similar to liquid soap. Kelp powder can then be incorporated into the mixture in a volumetric amount as described above, and also food grade colorant as desired to achieve a desired color for the mixture. The mixture can be further beat with the blender until a more viscous mixture is obtained, having a consistency approaching that of a cream. The mixture can then be poured into storage jars or containers (e.g., 3 oz. cosmetic jars) and allowed to stand for a sufficient period of time (e.g., about 4-12 hours) to achieve a desired thickness for the cream prior to use.

The cosmetic formulation can be applied as a cream to selected portions of the user's skin to treat the user's skin for a variety of applications. For example, the cosmetic formulation can be applied to moisturize the user's skin, to provide sunscreen protection, and to treat eczema or acne. In addition, the formulation can be used in varying amounts as a conditioner as well as a styling element for wet or dry hair of all grades and textures. It may also serve as a moisturizer for dry scalp conditions including relief of mild, non-systemic dandruff.

While some of the substances for the formulation are known for use in other cosmetic formulations, it is the unique combination of the substances in the concentration amounts described above that results in a cosmetic product believed to have unexpected and enhanced benefits.

Having described specific embodiments of novel cosmetic formulations, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed:

1. A formulation consisting essentially of water, shea butter, an emulsifier, myrrh, bergamot oil, sandalwood oil, orange oil, cocoa butter, coconut oil, kelp powder, and a preservative comprising a mixture of phenoxyethanol, methylparaben, ethylparaben, propylparaben and butylparaben.

2. The formulation of claim 1, wherein an amount of water in the formulation is from about 35% to about 50% by volume of the formulation, an amount of shea butter in the formulation is from about 25% to about 40% by volume of the formulation, an amount of emulsifier in the formulation is from about 10% to about 20% by volume of the formulation, an amount each of myrrh, orange oil, bergamot oil and sandalwood oil in the formulation is less than about 1% by volume of the formulation, an amount of cocoa butter in the formulation is no greater than about 10% by volume of the formulation, an amount of coconut oil in the formulation is no greater than about 5% by volume of the formulation, an amount of kelp powder in the formulation is less than about 1% by volume of the formulation, and an amount of the preservative in the formulation is less than about 2% by volume of the formulation.

3. A formulation consisting essentially of water, shea butter, an emulsifier, myrrh, bergamot oil, sandalwood oil, orange oil, cocoa butter, coconut oil, kelp powder, a colorant, and a preservative comprising a mixture of phenoxyethanol, methylparaben, ethylparaben, propylparaben and butylparaben.

4. The formulation of claim 3, wherein the colorant provides a green color for the formulation.

\* \* \* \* \*